US00PP17731P2

(12) United States Plant Patent
Whetman

(10) Patent No.: US PP17,731 P2
(45) Date of Patent: May 15, 2007

(54) ***DIANTHUS* PLANT NAMED 'DEVON FLORES'**

(50) Latin Name: *Dianthus×hybrida*
Varietal Denomination: DEVON FLORES

(76) Inventor: John Whetman, Deer Park Farm, Chudleigh, Devon (GB), TQ113ONH ( * ) Notice: Subject to any disclaimer, the term of this patent is extended or adjusted under 35 U.S.C. 154(b) by 27 days.

(21) Appl. No.: 11/274,011

(22) Filed: Nov. 14, 2005

(51) Int. Cl.
*A01H 5/00* (2006.01)

(52) U.S. Cl. ..... Plt./272; Plt./277; Plt./282

(58) Field of Classification Search ..... Plt./272
See application file for complete search history.

*Primary Examiner*—Anne Marie Grunberg
*Assistant Examiner*—S. B. McCormick-Ewoldt

(57) ABSTRACT

A new cultivar of *Dianthus* plant named 'DEVON FLORES' that is characterized by pronounced compact habit, grey-green foliage, and bright magenta flowers. In combination these traits set 'DEVON FLORES' apart from all other existing varieties of *Dianthus* known to the inventor.

1 Drawing Sheet

Genus: *Dianthus*. Species: ×*hybrida*.
Denomination: DEVON FLORES.

BACKGROUND OF THE INVENTION

The present invention relates to a new and distinct cultivar of carnation that is grown for use as a flowering plant for pots and containers. The new cultivar is known botanically as *Dianthus×hybrida* and will be referred to hereinafter by the cultivar name 'DEVON FLORES'.

'DEVON FLORES' is a complex hybrid plant that is the product of a breeding program started by the inventor in 1980. The breeding program is ongoing, conducted in a cultivated area of Houndspool, Dawlish, Devon, United Kingdom. The primary focus of the breeding program is to produce new cultivars of carnations that exhibit unique growth habit. The inventor selected 'DEVON FLORES' in 2001 for its unique pronounced compact habit accompanied by abundant bright magenta flowers that bloom from May through October.

'DEVON FLORES' is a dwarf carnation exhibiting pronounced compact habit, grey-green foliage, and bright magenta flowers. The colors of stems, leaves, calyx, and epicalyx are of material retaining the characteristic waxy bloom of *Dianthus*. 'DEVON FLORES' resulted from the open pollination between a number of different breeding lines, each of them a complex hybrid derived from *D. gratianopolitanus, D. plumarius* and others. The variety of *Dianthus* which is considered by the inventor to most closely resemble 'DEVON FLORES' is the inventor's variety *Dianthus* 'Devon Winnie' (U.S. Plant Pat. No. 14,893). 'DEVON FLORES' is very vigorous compared to the moderately vigorous 'Devon Winnie'. 'DEVON FLORES' has a stronger perfume and is a deeper magenta than 'Devon Winnie'.

Asexual reproduction of the new cultivar was first accomplished by the inventor in 2001 in a cultivated area of Houndspool, United Kingdom. The method of asexual propagation used was vegetative cuttings. Since that time the characteristics of the new cultivar have been determined stable and are reproduced true to type in successive generations of asexual reproduction.

SUMMARY OF THE INVENTION

The following traits have been repeatedly observed and represent the characteristics of the new *Dianthus* cultivar 'DEVON FLORES'. These traits in combination distinguish this cultivar from all other commercial varieties known to the inventor. 'DEVON FLORES' has not been tested under all possible conditions and phenotypic differences may be observed with variations in environmental, climatic and cultural conditions, however, without any variance in genotype.

1. *Dianthus* 'DEVON FLORES' exhibits a pronounced compact habit.
2. *Dianthus* 'DEVON FLORES' blooms profusely.
3. *Dianthus* 'DEVON FLORES' exhibits bright magenta flowers from May through October.
4. *Dianthus* 'DEVON FLORES' exhibits grey-green foliage.
5. At maturity, the height of the foliage mound of *Dianthus* 'DEVON FLORES' is 15 cm to 20 cm. The mature width is 20 cm to 30 cm.
6. *Dianthus* 'DEVON FLORES' is a perennial herb.
7. *Dianthus* 'DEVON FLORES' is suitable for use as a flowering plant in pots, containers, window boxes and the garden.
8. *Dianthus* 'DEVON FLORES' is hardy to minus 15° Centigrade.

BRIEF DESCRIPTION OF THE DRAWING

The accompanying color drawing illustrate the overall appearance of the new *Dianthus* variety 'DEVON FLORES' showing colors as true as it is reasonably possible to obtain in colored reproductions of this type. Colors in the drawing may differ from the color values cited in the detailed botanical description, which accurately describe the actual colors of the new variety 'DEVON FLORES'.

The drawing labeled as FIG. 1 depicts an entire flowering plant. The drawing was made of a plant grown in 1.5-liter container in a cold glasshouse in Devon, United Kingdom. No chemicals were used to treat the plant. The drawing was made using conventional techniques and although colors may appear different from actual colors due to light reflectance they are as accurate as possible by conventional photography.

BOTANICAL DESCRIPTION OF THE PLANT

Figure 1:
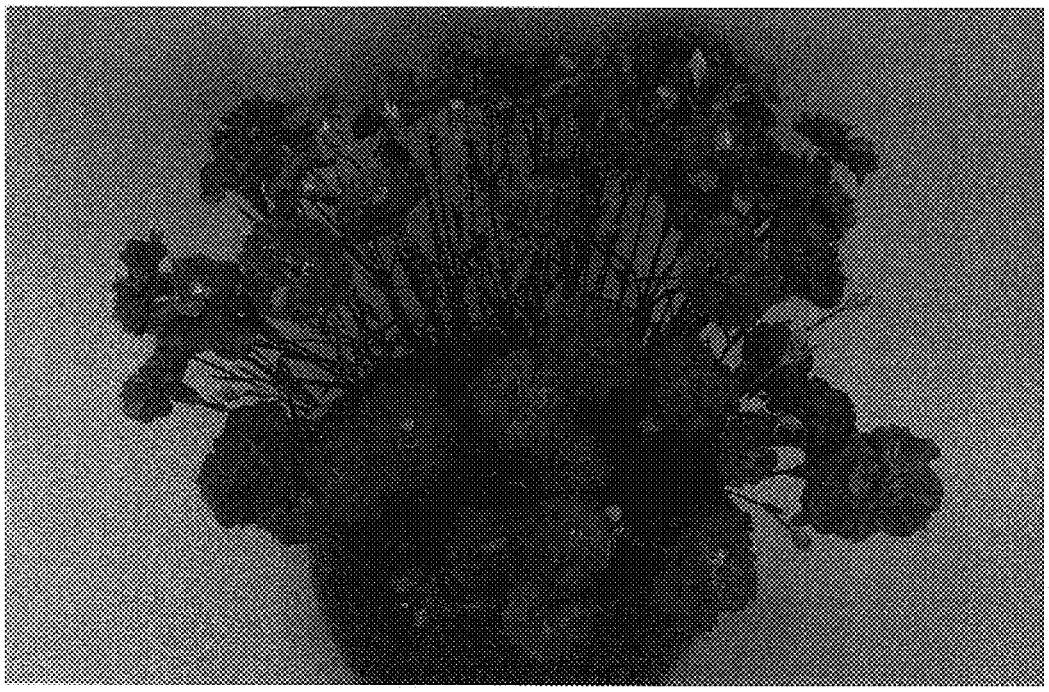

The following is a detailed description of the new cultivar 'DEVON FLORES'. Data was collected in spring from 1.5-liter container plants in spring, and grown indoors in Devon, United Kingdom. The color determinations are in accordance with the 2001 edition of The Royal Horticultural Society Colour Chart except where general color terms of ordinary dictionary significance are used. No chemicals were used to treat the plants. Growing conditions are typical to other *Dianthus.*

Botanical classification: *Dianthus* 'DEVON FLORES'.
Species: ×*Hybrida.*
Common name: Dwarf carnation.
Commercial classification: *Dianthus* hybrid.
Type: Perennial herb.
Use: Used as a flowering plant for pots and containers.
Parentage: 'DEVON FLORES' is a complex hybrid plant that resulted from the open pollination between *D. gratianopolitanus, D. plumarius,* and others.
Plant description:
- *Bloom period.*—May through October.
- *Plant habit.*—Pronounced compact habit.
- *Plant height.*—15 cm to 20 cm in height at maturity.
- *Plant width.*—20 cm to 30 cm in width at maturity.
- *Plant hardiness.*—Hardy to minus 15° Centigrade.
- *Root system.*—Fine fibrous roots.
- *Propagation.*—Propagation is accomplished using vegetative cuttings.
- *Cultural requirements.*—Grow in full sun in well-drained, moderately fertile soil.
- *Diseases and pests.*—Susceptible to known *Dianthus* pests and disease but no other susceptibilities to pests or disease are known to the inventor.
- *Time and temperature needed to produce a rooted cutting.*—2 weeks are needed to produce roots on cuttings using a mist propagation unit with bottom heat of 20° Centigrade, and a minimum air temperature of 15° Centigrade.
- *Crop time.*—An average of 3 months in the spring and 6 months in the fall is needed to produce a finished container size plant from a well-rooted cutting.

Stem:
- *Shape.*—Cylindrical.
- *Stem dimensions.*—100 mm to 120 mm in length, and 3 mm in diameter.
- *Stem surface.*—Glabrous and glaucous.
- *Stem color.*—135B.
- *Branching.*—Numerous branching shoots from the axils of lower leaves.
- *Internode length.*—8 mm to 10 mm. between nodes.
- *Node color.*—135B.
- *Node dimensions.*—5 mm. in diameter and 3 mm. in length.

Foliage:
- *Type.*—Evergreen.
- *Shape.*—Linear.
- *Division.*—Simple.
- *Apex.*—Acute.
- *Base.*—Decurrent.
- *Venation.*—Not Prominent.
- *Margins.*—Entire.
- *Attachment.*—Sheathing.
- *Arrangement.*—Opposite and spiraling up stem.
- *Surfaces* (*adaxial and abaxial*).—Glaucous.
- *Leaf dimensions.*—50 mm to 60 mm in length and an average of 4 mm in width.
- *Leaf color* (*adaxial and abaxial surfaces*).—N135A.
- *Fragrance.*—Absent.

Flowers:
- *Inflorescence.*—Cymose.
- *Flower type.*—Salviform, double and symmetrical.
- *Flower dimensions* (*including calyx*).—30 mm in length and 30 in diameter.
- *Fragrance.*—Strong.
- *Bud color.*—N138C.
- *Anthocyanin.*—Present.
- *Bud dimensions.*—20 mm in length and 8 mm in width.
- *Bud shape.*—Cylindrical.
- *Petals.*—Persistent, apopetalous, overlapping.
- *Petal number.*—Five petals.
- *Petal margin.*—Crenate-denate.
- *Petal shape.*—Obteltoid.
- *Petal surface.*—Glabrous.
- *Petal dimensions.*—30 mm. in length and 25 mm. in width.
- *Ground color of blade.*—N78A.
- *Color of band around center.*—N79A.
- *Color of middle of strap.*—145B.
- *Color of base of strap.*—145D.
- *Calyx dimensions.*—7 mm in diameter and 20 mm in length.
- *Calyx color.*—133B.
- *Anthocynanin.*—Absent.
- *Sepals.*—Five in number.
- *Fused or unfused.*—Sepals fused.
- *Sepal color.*—133B.
- *Anthocyanin.*—Absent.
- *Peduncle dimensions*—150 mm in length and 2 mm in diameter.
- *Peduncle color.*—N138C.
- *Peduncle surface.*—Glaucous.
- *Epicalyx.*—Present.
- *Bracts.*—One pair in number (2 individual bracts).
- *Bract dimensions.*—5 mm in width and 5 mm in length.
- *Bract color.*—133B.
- *Anthocyanin.*—Absent.
- *Bracteoles.*—1 pair (2 individual bracteoles).
- *Dimensions.*—3 mm in width, 5 mm in length.
- *Anthocyanin.*—Absent.
- *Stipules.*—Two per node.
- *Stipule dimensions.*—A range of 3 mm–5 mm. in width and a range of 7 mm–35 mm in length.
- *Stipule color.*—139C.
- *Anthocyanin.*—Present.
- *Lastingness of flower.*—Each individual flower lasts an average of 10 days at 20° centigrade.

Reproductive organs:
- *Stamens.*—5 but variable and often petaloid.
- *Stamen dimensions.*—18 mm to 29 mm in length and 0.5 mm in diameter.
- *Stamen color.*—Upper 78D, lower white.
- *Anther number.*—5 usually aborted.

*Anther attachment.*—Dorsifixed.
*Anther color.*—78D.
*Anther dimensions.*—2 mm in length and 1 mm in diameter.
*Pollen.*—Absent.
*Pistil.*—One that divides into two above the ovary.
*Pistil dimensions.*—37 mm. in length.
*Styles.*—Two in number.
*Style dimensions.*—20 mm in length and 1 mm in diameter.
*Style color.*—78D.
*Stigma number.*—Single.
*Stigma shape.*—A single stigma.
*Color of stigma.*—63D.
*Height above petals.*—15 mm above petals.
*Ovary position.*—Superior.
*Ovary dimensions.*—5 mm in length and 3 mm in diameter.
*Ovary shape.*—Spindle shaped.
*Ovary color.*—Colors 141C and 144C are individually present on an individual ovary.
Seed: Seed: Absent.

It is claimed:

1. A new and distinct cultivar of *Dianthus* plant named 'DEVON FLORES' as described and illustrated herein.

* * * * *